(12) United States Patent
Locke et al.

(10) Patent No.: US 10,556,043 B2
(45) Date of Patent: Feb. 11, 2020

(54) REDUCED-PRESSURE, MULTI-ORIENTATION, LIQUID-COLLECTION CANISTER

(71) Applicant: KCI Licensing, Inc., San Antonio, TX (US)

(72) Inventors: Christopher Brian Locke, Bournemouth (GB); James A. Luckemeyer, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 432 days.

(21) Appl. No.: 15/261,094

(22) Filed: Sep. 9, 2016

(65) Prior Publication Data

US 2016/0375181 A1    Dec. 29, 2016

Related U.S. Application Data

(63) Continuation of application No. 13/211,172, filed on Aug. 16, 2011, now Pat. No. 9,463,265.
(Continued)

(51) Int. Cl.
*A61M 1/00* (2006.01)

(52) U.S. Cl.
CPC ........ *A61M 1/0001* (2013.01); *A61M 1/0049* (2013.01); *A61M 1/0052* (2014.02);
(Continued)

(58) Field of Classification Search
CPC combination set(s) only.
See application file for complete search history.

(56) References Cited

U.S. PATENT DOCUMENTS 1,355,846 A * 10/1920 Rannells ............. A61F 13/2048
604/286
2,547,758 A    4/1951 Keeling
(Continued)

FOREIGN PATENT DOCUMENTS

AU        550575 B2     3/1986
AU        745271 B2     3/2002
(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery.
(Continued)

*Primary Examiner* — Ophelia A Hawthorne
*Assistant Examiner* — Guy K Townsend

(57) ABSTRACT

An apparatus for use in a multi-orientation liquid collection canister to collect liquid from a tissue site is provided. The apparatus includes a substantially planar, liquid-air separator disposed on at least one wall of the multi-orientation liquid collection canister to prevent the liquid from exiting the multi-orientation liquid collection canister. The apparatus further includes an elongated member connected to the liquid-air separator and extending away from the liquid-air separator into a first space of the multi-orientation liquid collection canister. The elongated member has a membrane defining a second space along at least a portion of a length of the elongated member. At least a portion of the membrane allows gaseous communication between the first space and the second space.

40 Claims, 10 Drawing Sheets

Related U.S. Application Data

(60) Provisional application No. 61/374,995, filed on Aug. 18, 2010.

(52) U.S. Cl.
CPC ......... *A61M 1/0096* (2014.02); *A61M 1/0088* (2013.01); *A61M 2205/7536* (2013.01)

(56) References Cited

U.S. PATENT DOCUMENTS

| | | | |
|---|---|---|---|
| 2,632,443 A * | 3/1953 | Lesher | A61F 13/00021 128/888 |
| 2,682,873 A * | 7/1954 | Evans | A61F 13/00029 602/42 |
| 2,910,763 A * | 11/1959 | Lauterbach | D04H 1/06 442/405 |
| 2,969,057 A | 1/1961 | Simmons | |
| 3,066,672 A | 12/1962 | Crosby, Jr. et al. | |
| 3,367,332 A * | 2/1968 | Groves | A61F 13/00068 604/290 |
| 3,520,300 A * | 7/1970 | Flower, Jr. | A61M 1/008 604/269 |
| 3,568,675 A * | 3/1971 | Harvey | A61M 1/0088 604/355 |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A * | 3/1981 | Nichols | A61M 1/005 137/202 |
| 4,261,363 A * | 4/1981 | Russo | A61M 25/02 128/200.26 |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A * | 5/1983 | Svedman | A61F 13/00068 604/114 |
| 4,392,853 A | 7/1983 | Muto | |
| 4,392,858 A * | 7/1983 | George | A61M 1/0011 604/126 |
| 4,419,097 A | 12/1983 | Rowland | |
| 4,465,485 A * | 8/1984 | Kashmer | A61M 1/0052 128/205.12 |
| 4,475,909 A | 10/1984 | Eisenberg | |
| 4,480,638 A * | 11/1984 | Schmid | A61F 5/34 128/118.1 |
| 4,525,166 A | 6/1985 | Leclerc | |
| 4,525,374 A | 6/1985 | Vaillancourt | |
| 4,540,412 A * | 9/1985 | Van Overloop | A61F 7/02 604/291 |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A * | 8/1986 | Weston | A61M 35/00 424/449 |
| 4,608,041 A | 8/1986 | Nielsen | |
| 4,640,688 A | 2/1987 | Hauser | |
| 4,655,754 A * | 4/1987 | Richmond | A61M 1/0056 137/197 |
| 4,664,662 A | 5/1987 | Webster | |
| 4,710,165 A * | 12/1987 | McNeil | A61M 1/0023 604/31 |
| 4,733,659 A | 3/1988 | Edenbaum et al. | |
| 4,743,232 A * | 5/1988 | Kruger | A61F 13/023 128/DIG. 26 |
| 4,758,220 A | 7/1988 | Sundblom et al. | |
| 4,787,888 A | 11/1988 | Fox | |
| 4,826,494 A * | 5/1989 | Richmond | A61M 1/0056 604/126 |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A * | 3/1990 | Reed | A61F 13/023 602/46 |
| 4,919,654 A | 4/1990 | Kalt | |
| 4,941,882 A * | 7/1990 | Ward | A61F 13/023 128/DIG. 26 |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A * | 3/1992 | Benson | A61M 1/0096 604/319 |
| 5,100,396 A | 3/1992 | Zamierowski | |
| 5,134,994 A * | 8/1992 | Say | A61M 1/0023 128/200.24 |
| 5,149,331 A | 9/1992 | Ferdman et al. | |
| 5,167,613 A * | 12/1992 | Karami | A61F 13/0203 602/42 |
| 5,176,663 A * | 1/1993 | Svedman | A61F 13/0203 128/888 |
| 5,215,522 A | 6/1993 | Page et al. | |
| 5,232,453 A | 8/1993 | Plass et al. | |
| 5,261,893 A * | 11/1993 | Zamierowski | A61F 5/453 128/DIG. 26 |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A * | 8/1995 | Todd | A61M 1/0088 15/420 |
| 5,527,293 A | 6/1996 | Zamierowski | |
| 5,549,584 A * | 8/1996 | Gross | A61M 1/0088 604/313 |
| 5,556,375 A | 9/1996 | Ewall | |
| 5,607,388 A | 3/1997 | Ewall | |
| 5,636,643 A * | 6/1997 | Argenta | A61M 1/0088 128/897 |
| 5,645,081 A * | 7/1997 | Argenta | A61M 1/0088 128/897 |
| 6,071,267 A * | 6/2000 | Zamierowski | A61F 13/0203 604/289 |
| 6,093,230 A * | 7/2000 | Johnson, III | A61M 1/0049 55/482 |
| 6,135,116 A * | 10/2000 | Vogel | A61F 13/069 128/898 |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 * | 4/2003 | Heaton | A61F 13/023 128/897 |
| 6,648,862 B2 * | 11/2003 | Watson | A61M 1/0001 604/319 |
| 6,814,079 B2 * | 11/2004 | Heaton | A61F 13/023 128/897 |
| 7,524,286 B2 * | 4/2009 | Johnson | A61B 5/14542 600/304 |
| 7,846,141 B2 | 12/2010 | Weston | |
| 8,062,273 B2 | 11/2011 | Weston | |

(56) References Cited

U.S. PATENT DOCUMENTS

| | | | |
|---|---|---|---|
| 8,172,818 B2* | 5/2012 | Locke | A61M 1/0001 604/319 |
| 8,177,763 B2* | 5/2012 | Wiesner | A61M 1/0049 604/313 |
| 8,216,198 B2 | 7/2012 | Heagle et al. | |
| 8,251,979 B2 | 8/2012 | Malhi | |
| 8,257,327 B2 | 9/2012 | Blott et al. | |
| 8,398,614 B2 | 3/2013 | Blott et al. | |
| 8,449,509 B2 | 5/2013 | Weston | |
| 8,529,548 B2 | 9/2013 | Blott et al. | |
| 8,535,296 B2 | 9/2013 | Blott et al. | |
| 8,551,060 B2 | 10/2013 | Schuessler et al. | |
| 8,568,386 B2 | 10/2013 | Malhi | |
| 8,679,081 B2 | 3/2014 | Heagle et al. | |
| 8,834,451 B2 | 9/2014 | Blott et al. | |
| 8,926,592 B2 | 1/2015 | Blott et al. | |
| 9,017,302 B2 | 4/2015 | Vitaris et al. | |
| 9,198,801 B2 | 12/2015 | Weston | |
| 9,211,365 B2 | 12/2015 | Weston | |
| 9,289,542 B2 | 3/2016 | Blott et al. | |
| 9,463,265 B2* | 10/2016 | Locke | A61M 1/0001 |
| 2002/0077661 A1* | 6/2002 | Saadat | A61B 17/08 606/221 |
| 2002/0099343 A1* | 7/2002 | Garcia | A61M 1/0023 604/313 |
| 2002/0115951 A1* | 8/2002 | Norstrem | A61F 5/0111 602/27 |
| 2002/0120185 A1* | 8/2002 | Johnson | A61B 5/14542 600/364 |
| 2002/0143286 A1* | 10/2002 | Turney | A61B 5/445 604/11 |
| 2003/0093041 A1* | 5/2003 | Risk, Jr. | A61M 27/00 604/308 |
| 2003/0178360 A1* | 9/2003 | Haldopoulos | A61M 1/0001 210/435 |
| 2004/0122434 A1* | 6/2004 | Argenta | A61B 17/88 606/86 R |
| 2004/0167482 A1* | 8/2004 | Watson | A61M 1/0001 604/317 |
| 2004/0225208 A1* | 11/2004 | Johnson | A61B 5/14542 600/364 |
| 2009/0204084 A1* | 8/2009 | Blott | A61M 1/0058 604/290 |
| 2009/0227969 A1* | 9/2009 | Jaeb | A61M 1/0088 604/313 |
| 2009/0240185 A1* | 9/2009 | Jaeb | A61M 1/0088 602/48 |
| 2009/0292264 A1 | 11/2009 | Hudspeth et al. | |
| 2009/0306630 A1* | 12/2009 | Locke | A61M 1/0001 604/543 |
| 2010/0063463 A1* | 3/2010 | Wiesner | A61M 1/0049 604/313 |
| 2010/0106115 A1* | 4/2010 | Hardman | A61M 1/0088 604/319 |
| 2010/0286638 A1 | 11/2010 | Malhi | |
| 2014/0163491 A1 | 6/2014 | Schuessler et al. | |
| 2015/0080788 A1 | 3/2015 | Blott et al. | |
| 2016/0375181 A1* | 12/2016 | Locke | A61M 1/0001 604/319 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 01/37922 A2 | 5/2001 |
| WO | 2009016195 A2 | 2/2009 |
| WO | 20090111341 A2 | 9/2009 |
| WO | WO-2009111341 A2* | 9/2009 |
| WO | 2009149250 A1 | 12/2009 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 pages English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

(56) References Cited

OTHER PUBLICATIONS

Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
A Živadinovi?, V. ?uki?, Ž. Maksimovi?, ?. Radak, and P. Peš ka, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.
Extended European Search Report for corresponding Application No. 16192619, dated Jan. 20, 2017.
Chinese First Office Action for Corresponding Application No. 2017105612807, dated Mar. 21, 2019.

* cited by examiner

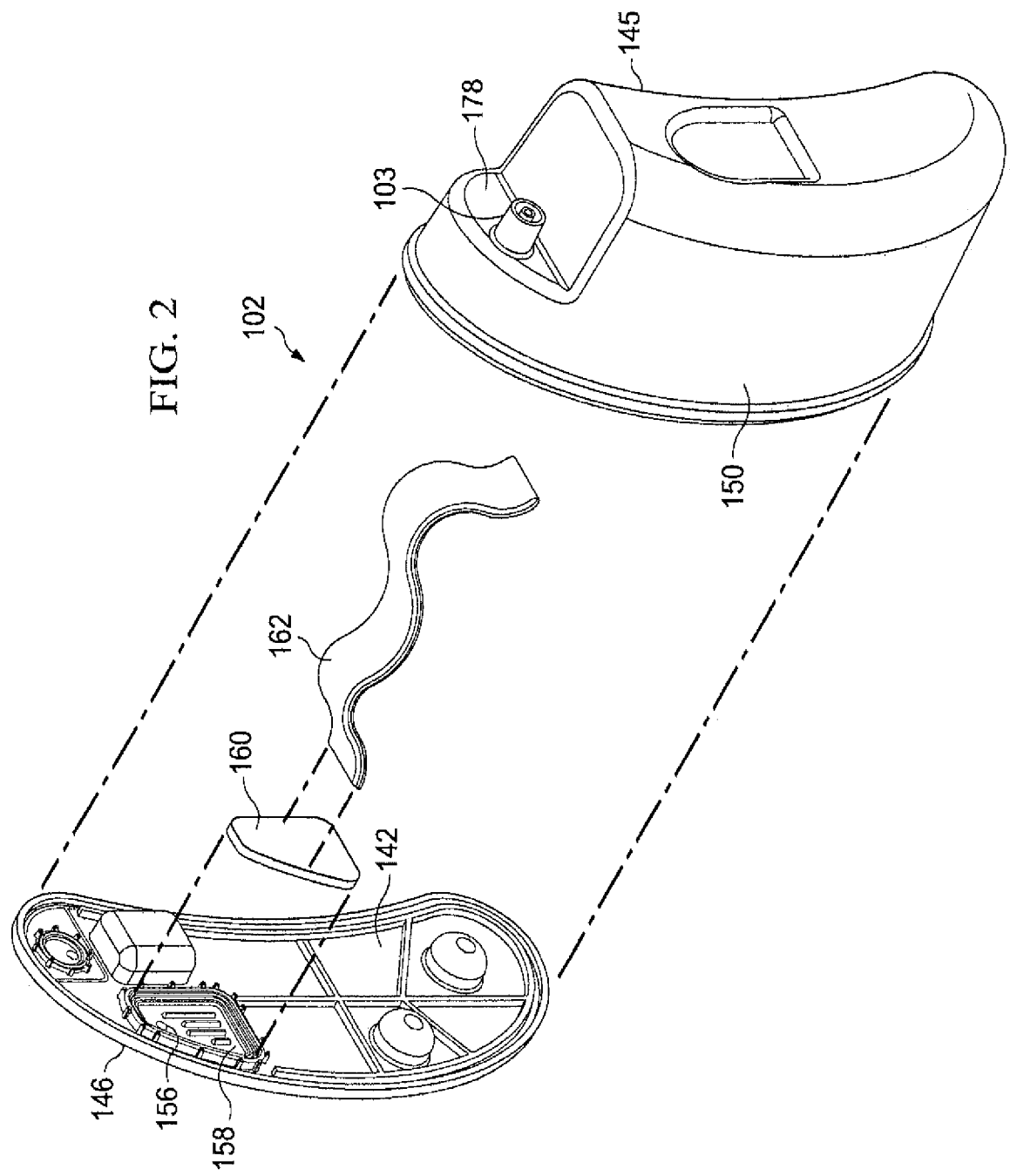

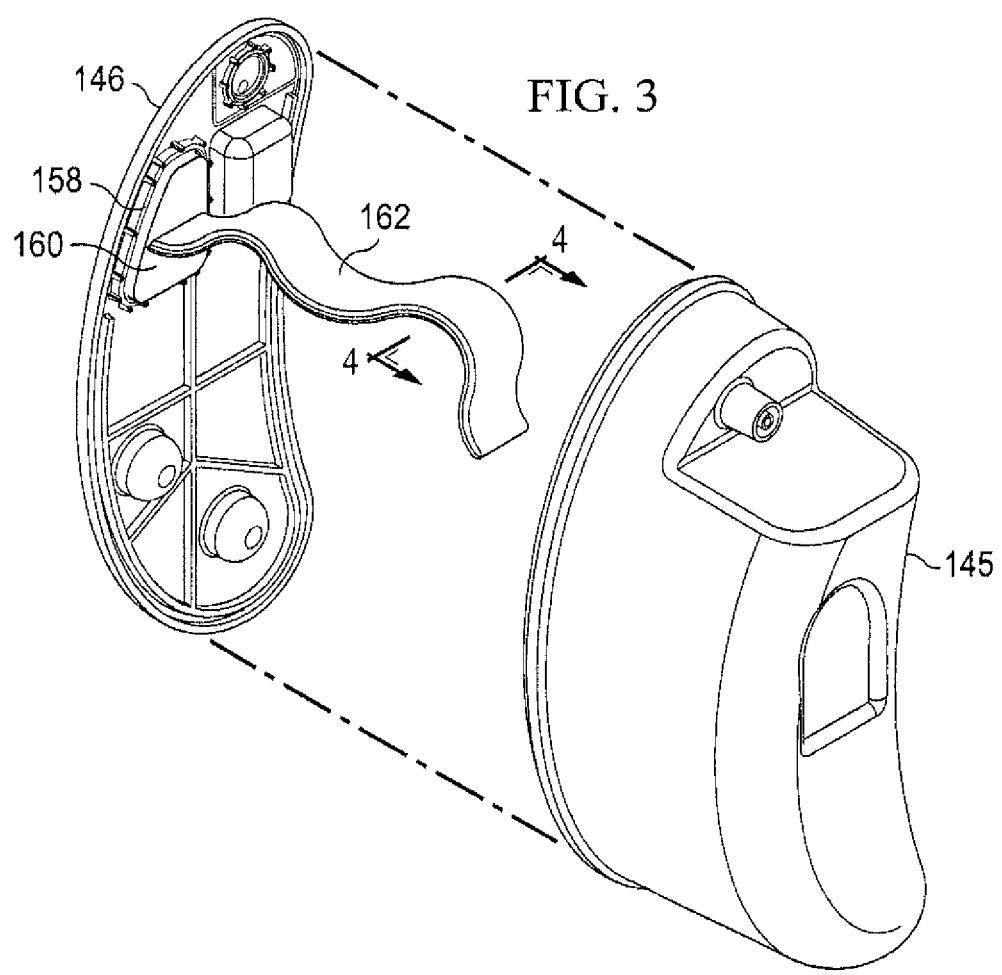

REDUCED-PRESSURE, MULTI-ORIENTATION, LIQUID-COLLECTION CANISTER

CROSS-REFERENCE TO RELATED APPLICATIONS

This application is a continuation of U.S. patent application Ser. No. 13/211,172, filed Aug. 16, 2011, which claims the benefit of U.S. Provisional Application No. 61/374,995, filed Aug. 18, 2010, which is hereby incorporated by reference.

BACKGROUND OF THE INVENTION

1. Field of the Invention

The present invention relates generally to reduced pressure treatment systems and more particularly to a reduced-pressure, liquid-collection canister having a filter that allows operation of the canister in multiple orientations.

2. Description of Related Art

Clinical studies and practice have shown that providing a reduced pressure in proximity to a tissue site augments and accelerates the growth of new tissue at the tissue site. The applications of this phenomenon are numerous, but one particular application of reduced pressure involves treating wounds. This treatment (frequently referred to in the medical community as "negative pressure wound therapy," "reduced pressure therapy," or "vacuum therapy") provides a number of benefits, including migration of epithelial and subcutaneous tissues cells, improved blood flow, and micro-deformation of tissue at the wound site. Together these benefits result in increased development of granulation tissue and faster healing times. Typically, reduced pressure is applied by a reduced pressure source to tissue through a porous pad or other manifold device. In many instances, wound exudate and other liquids from the tissue site are collected within a canister to prevent the liquids from reaching the reduced pressure source.

SUMMARY

The problems presented by existing reduced pressure systems and liquid collection canisters are solved by the systems and methods of the illustrative embodiments described herein. A reduced pressure treatment system for applying reduced pressure treatment to a tissue site includes a reduced pressure source, a liquid-collection canister, and a manifold positioned at the tissue site and in fluid communication with the liquid-collection canister. In one embodiment, the liquid-collection canister includes at least one canister wall defining a first space configured to collect liquid from the tissue site. A canister outlet is configured to allow communication between the reduced pressure source and the first space. A substantially planar, liquid-air separator is disposed adjacent the canister outlet to prevent the liquid from exiting the first space through the canister outlet. An elongated member is connected to the liquid-air separator and extends away from the liquid-air separator into the first space. The elongated member has a membrane defining a second space along at least a portion of a length of the elongated member, and at least a portion of the membrane allows gaseous communication between the first space and the second space.

In another embodiment, an apparatus for use in a multi-orientation liquid collection canister to collect liquid from a tissue site is provided. The apparatus includes an elongated member configured for fluid connection to an outlet of the liquid collection canister. The elongated member having a membrane defining a space along at least a portion of a length of the elongated member, and at least a portion of the membrane allows gaseous communication, but substantially prevents liquid communication through the at least a portion of the membrane.

In yet another embodiment, a reduced pressure treatment system for applying reduced pressure treatment to a tissue site is provided. The system includes a reduced pressure source, a liquid-collection canister, and a manifold positioned at the tissue site and in fluid communication with the liquid-collection canister. The liquid-collection canister includes a chamber configured to collect liquid from the tissue site. A canister outlet is in fluid communication with the reduced pressure source. The liquid-collection canister further includes a flexible member having a gas communication pathway at least partially defined by a flexible membrane. The flexible member is positioned in the chamber such that the gas communication pathway is in fluid communication with the canister outlet and at least a portion of the flexible membrane is gas permeable and substantially liquid impermeable.

Still, in another embodiment, a liquid-collection canister for collecting liquid from a tissue site is provided. The liquid-collection canister includes a chamber configured to collect liquid from the tissue site. A canister outlet is in fluid communication with the reduced pressure source. The liquid-collection canister further includes a flexible member having a gas communication pathway at least partially defined by a flexible membrane. The flexible member is positioned in the chamber such that the gas communication pathway is in fluid communication with the canister outlet and at least a portion of the flexible membrane is gas permeable and substantially liquid impermeable.

In another embodiment, an apparatus is provided for use in a multi-orientation liquid collection canister to collect liquid from a tissue site to which reduced pressure treatment is applied. The apparatus includes a flexible member configured for fluid connection to an outlet of the liquid-collection canister. The flexible member having a gas communication pathway at least partially defined by a flexible membrane. The gas communication pathway is adapted to be positioned in fluid communication with the canister outlet and at least a portion of the flexible membrane is gas-permeable and substantially liquid impermeable.

In yet another embodiment, a reduced pressure treatment system for applying reduced pressure treatment to a tissue site is provided. The system includes a reduced pressure source, a liquid-collection canister, and a manifold positioned at the tissue site and in fluid communication with the liquid-collection canister. The liquid-collection canister includes at least one canister wall defining a chamber configured to collect liquid from the tissue site. A canister outlet is in fluid communication with the reduced pressure source. A conduit is positioned in the chamber. The conduit has a conduit wall forming a gas communication lumen. The gas-communication lumen is fluidly connected to the canister outlet. A liquid-air separator is operably associated with the conduit to allow gas communication, but substantially prevents liquid communication between the chamber and the gas-communication lumen.

In still another embodiment, an apparatus is provided for use in a multi-orientation liquid collection canister to collect liquid from a tissue site to which reduced pressure treatment is applied. The apparatus includes a conduit adapted to fluidly connect to an outlet of the liquid-collection canister.

The conduit having a gas-communication lumen at least partially defined by a conduit wall. A liquid-air separator is operably associated with the conduit to allow gas-communication, but substantially prevents liquid communication between the gas-communication lumen and an area surrounding the conduit.

In still another embodiment, a method is provided for retrofitting a wound fluid collection canister to allow collection of wound fluid in multiple orientations of the wound fluid collection canister. The method includes fluidly connecting an elongated member to an outlet of the wound fluid collection canister. At least a portion of the elongated member extends into a liquid collection area of the wound fluid collection canister. The method further includes allowing gas exchange between an inner space of the elongated member and the liquid collection area; and substantially preventing liquid exchange between the inner space and the liquid collection area.

Other objects, features, and advantages of the illustrative embodiments will become apparent with reference to the drawings and detailed description that follow.

BRIEF DESCRIPTION OF THE DRAWINGS

FIG. 2 illustrates an exploded perspective view of the liquid-collection canister of FIG. 1 and filter elements associated with the liquid-collection canister according to an illustrative embodiment;

FIG. 3 illustrates a perspective view of the filter element connected to a base of the liquid-collection canister of FIG. 2;

DETAILED DESCRIPTION OF ILLUSTRATIVE EMBODIMENTS

In the following detailed description of several illustrative embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

The term "reduced pressure" as used herein generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure associated with tissue at the tissue site. Although the terms "vacuum" and "negative pressure" may be used to describe the pressure applied to the tissue site, the actual pressure reduction applied to the tissue site may be significantly less than the pressure reduction normally associated with a complete vacuum. Reduced pressure may initially generate fluid flow in the area of the tissue site. As the hydrostatic pressure around the tissue site approaches the desired reduced pressure, the flow may subside, and the reduced pressure is then maintained. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

The term "tissue site" as used herein refers to a wound or defect located on or within any tissue, including but not limited to, bone tissue, adipose tissue, muscle tissue, neural tissue, dermal tissue, vascular tissue, connective tissue, cartilage, tendons, or ligaments. The term "tissue site" may further refer to areas of any tissue that are not necessarily wounded or defective, but are instead areas in which it is desired to add or promote the growth of additional tissue. For example, reduced pressure tissue treatment may be used in certain tissue areas to grow additional tissue that may be harvested and transplanted to another tissue location.

Figure 1:
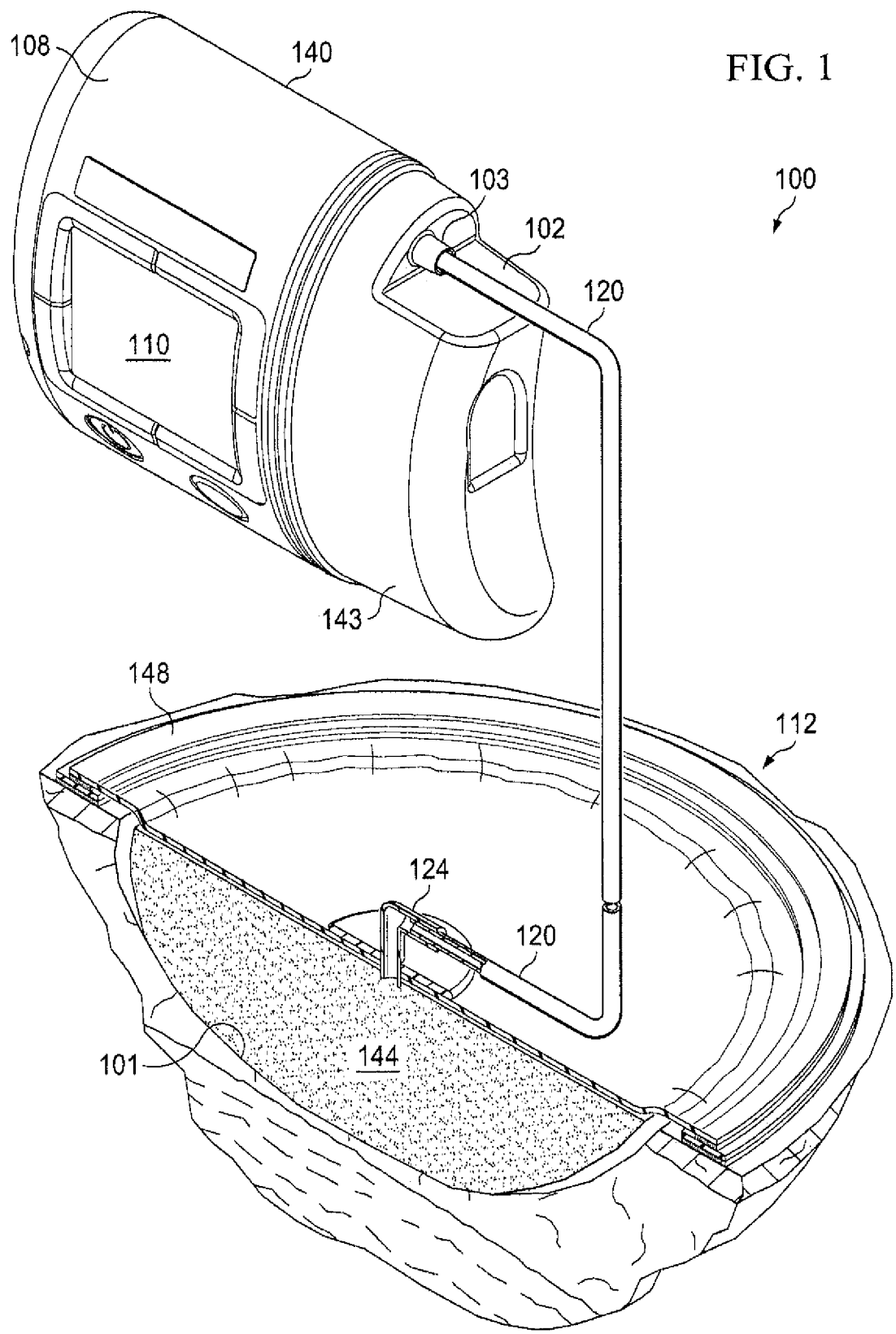
FIG. 1 illustrates a perspective view of a reduced pressure treatment system having a reduced pressure treatment unit and a multi-orientation, liquid-collection canister according to an illustrative embodiment.

Referring to FIG. 1, a reduced pressure treatment system 100 for applying a reduced pressure to a tissue site 101 of a patient according to an illustrative embodiment includes a canister 102 in fluid communication with a reduced pressure source 108 and a reduced pressure dressing 112 that is positioned at the tissue site 101. The reduced pressure dressing 112 is fluidly connected to an inlet 103 of the canister 102 by a conduit 120. The conduit 120 may fluidly communicate with the reduced pressure dressing 112 through a tubing adapter 124.

In at least one embodiment described herein, the canister 102 used to collect exudate or other fluids from the tissue site 101 is configured to allow the canister 102 to operate in multiple orientations even as the canister 102 begins to fill with liquid. The canister 102 preferably includes a protected gas communication pathway, or dry space, that allows continued gas communication with a liquid collection chamber 104 of the canister 102 as exudate and other liquids collect within the liquid collection chamber 104. The path of fluid communication in the reduced pressure treatment system 100 is as follows. Reduced pressure is supplied to the gas communication pathway of the canister 102 by the reduced pressure source 108. Typically this occurs by the reduced pressure source 108 drawing gaseous fluids, such as air, from the gas communication pathway. As the pressure within the gas communication pathway falls, gas flows from the liquid collection chamber 104 of the canister 102 to the gas communication pathway, thus resulting in a drop in pressure within the liquid collection chamber 104. Liquid is prevented from flowing into the gas communication pathway by a hydrophobic element, an oleophobic element, or some other type of liquid-blocking membrane, liquid-air separator, or other device. The reduced pressure within the liquid collection chamber 104 is transmitted to the dressing 112 at the tissue site 101, which allows fluids (both gases and liquids) to flow from the tissue site 101 to the liquid collection chamber 104. The liquid collects within the liquid collection chamber 104. In some embodiments, multiple fluid communication ports between the liquid collection chamber 104 and the gas communication pathway allow continued gaseous communication between the liquid collection chamber 104 and the gas communication pathway even as the liquid collection chamber 104 fills with liquids and blocks some of these communication ports. This configuration permits continued supply of reduced pressure to the liquid collection chamber 104 until the liquid collection canister is almost completely full of liquid. As an alternative to the multiple ports, a large common port may be provided so that only a portion of the port is covered or blocked by liquid as the canister 102 fills.

In the embodiment illustrated in FIG. 1, the reduced pressure source 108 is an electrically-driven vacuum pump. In another implementation, the reduced pressure source 108 may instead be a manually-actuated or manually-charged pump that does not require electrical power. The reduced pressure source 108 instead may be any other type of reduced pressure pump, or alternatively a wall suction port such as those available in hospitals and other medical facilities. The reduced pressure source 108 may be housed within or used in conjunction with a reduced pressure treatment unit 140, which may also contain sensors, processing units, alarm indicators, memory, databases, software, display units, and user interfaces 110 that further facilitate the application of reduced pressure treatment to the tissue site 101. In one example, a sensor or switch (not shown) may be disposed at or near the reduced pressure source 108 to determine a source pressure generated by the reduced pressure source 108. The sensor may communicate with a processing unit that monitors and controls the reduced pressure that is delivered by the reduced pressure source 108.

The reduced pressure dressing 112 includes a distribution manifold 144 adapted to be positioned at the tissue site 101, and a cover 148, or drape, that is positioned over the distribution manifold 144 to maintain reduced pressure beneath the cover 148 at the tissue site 101. The cover 148 may extend beyond a perimeter of the tissue site 101 and may include an adhesive or bonding agent on the cover 148 to secure the cover 148 to tissue adjacent the tissue site 101. In one embodiment, the adhesive disposed on cover 148 may be used to seal between the tissue and the cover 148 to prevent leakage of reduced pressure from the tissue site 101. In another embodiment, a seal layer (not shown) such as, for example, a hydrogel or other material may be disposed between the cover 148 and the tissue to augment or substitute for the sealing properties of the adhesive.

The distribution manifold 144 of the reduced pressure dressing 112 is adapted to contact the tissue site 101. The distribution manifold 144 may be partially or fully in contact with the tissue site 101 being treated by the reduced pressure dressing 112. When the tissue site 101 is a wound, the distribution manifold 144 may partially or fully fill the wound.

The distribution manifold 144 may be any size, shape, or thickness depending on a variety of factors, such as the type of treatment being implemented or the nature and size of the tissue site 101. For example, the size and shape of the distribution manifold 144 may be customized by a user to cover a particular portion of the tissue site 101, or to fill or partially fill the tissue site 101. The distribution manifold 144 may have, for example, a square shape, or may be shaped as a circle, oval, polygon, an irregular shape, or any other shape.

In one illustrative embodiment, the distribution manifold 144 is a foam material that distributes reduced pressure to the tissue site 101 when the distribution manifold 144 is in contact with or near the tissue site 101. The foam material may be either hydrophobic or hydrophilic. In one non-limiting example, the distribution manifold 144 is an open-cell, reticulated polyurethane foam such as GranuFoam® dressing available from Kinetic Concepts, Inc. of San Antonio, Tex.

In the example in which the distribution manifold 144 is made from a hydrophilic material, the distribution manifold 144 also functions to wick fluid away from the tissue site 101, while continuing to provide reduced pressure to the tissue site 101 as a manifold. The wicking properties of the distribution manifold 144 draw fluid away from the tissue site 101 by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated (including plasma treatment) or coated to provide hydrophilicity. In still another embodiment, the distribution manifold 144 may be a non-woven material such as Libeltex™ TDL2, manufactured by Libeltex Group.

The distribution manifold 144 may further promote granulation at the tissue site 101 when a reduced pressure is applied through the reduced pressure dressing 112. For example, any or all of the surfaces of the distribution manifold 144 may have an uneven, coarse, or jagged profile that causes microstrains and stresses at the tissue site 101 when reduced pressure is applied through the distribution manifold 144. These microstrains and stresses have been shown to increase new tissue growth.

In one embodiment, the distribution manifold 144 may be constructed from bioresorbable materials that do not have to be removed from a patient's body following use of the reduced pressure dressing 112. Suitable bioresorbable materials may include, without limitation, a polymeric blend of polylactic acid (PLA) and polyglycolic acid (PGA). The polymeric blend may also include without limitation polycarbonates, polyfumarates, and capralactones. The distribution manifold 144 may further serve as a scaffold for new cell-growth, or a scaffold material may be used in conjunction with the distribution manifold 144 to promote cell-growth. A scaffold is a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

Referring now to FIGS. 1 and 2, the canister 102 includes a canister housing 143 having a basin portion 145 and a lid portion 146. The lid portion 146 may be formed by an exit wall 142 that is substantially planar and is capable of mating with the basin portion 145 to form the liquid collection chamber 104. While the basin portion 145 is formed from a basin wall 150 that includes curved contours to create a crescent shape, the basin portion 145 and lid portion 146 may instead form a canister that is cylindrical, cubical, spherical, rectangular cubical, or any other shape. It should also be noted that the canister 102 may not include separate basin and lid portions, but rather may be formed from a substantially unitary housing. In such an embodiment, the liquid-collection chamber 104 may be defined by a single wall. Alternatively, the liquid-collection chamber 104 may be formed by a plurality of walls.

The canister 102 includes the inlet 103 that is fluidly connected to the conduit 120, a canister outlet 156 that is fluidly connected to the reduced pressure source 108, and a substantially planar liquid-air separator 160 that is operatively associated with the outlet 156 to prevent liquid from exiting the canister 102 through the canister outlet 156. The inlet 103 may be positioned on a wall 178 disposed in a recessed region of the basin portion 145. In one embodiment, the outlet 156 is positioned in the exit wall 142, and the substantially planar liquid-air separator 160 is positioned adjacent to the outlet 156 and secured to the exit wall 142. In some embodiments, the exit wall 142 may include a recessed region 158 that aids in providing a secure connection for the liquid-air separator 160. The outlet 156 allows fluid communication between the canister 102 and the reduced pressure source 108 such that a reduced pressure is capable of being maintained within the canister 102. This reduced pressure is capable of being transmitted to the tissue site through the inlet 103, the conduit 120, the tubing adapter 124, and the distribution manifold 144. The reduced pressure draws exudate and other fluids from the tissue site 101 into the canister 102. The substantially planar liquid-air separator 160 prevents liquids that that are drawn into the canister 102 from exiting the canister 102 through the outlet 156 and contaminating the reduced pressure source 108.

In an illustrative embodiment, the substantially planar liquid-air separator 160 may be a hydrophobic or oleophobic filter that prevents passage of liquids through the outlet 156. An example of a suitable hydrophobic material includes an expanded PTFE laminate such as a hydrophobic medical membrane manufactured by WL Gore & Associates, Newark, Del.; the Aspire® ePTFE filter membrane manufactured by General Electric; or any other suitable membrane. In one embodiment, such a laminate may have a 1.0 micron reference pore size on non woven polyester with a thickness range of 0.17 mm-0.34 mm. The hydrophobic medical membrane may have a minimum air flow of 18 LPM/cm$^2$ @ 1 bar (15 PSI) and a minimum water entry pressure of 1.1 bar (16.0 PSI). An example of a suitable oleophobic material includes an oleophobic expanded PTFE membrane having a 1.0 micron reference pore size on non woven polyester with a thickness range of 0.15 mm-0.39 mm. The oleophobic membrane may have a minimum air flow of 12 LPM/cm$^2$ @ 1 bar (15 PSI) and a minimum water entry pressure of 0.8 bar (12.0 PSI). Alternatively, the substantially planar liquid-air separator 160 may be a gravity-based barrier system, or a device that includes a hydrophilic surface to encourage condensation or other separation of liquid from a fluid stream when the fluid stream passes over the surface. Other examples of liquid-air separators 160 may include sintered metals, sintered nylons, specialty fiber filters such as those manufactured by Filtrona, plastics that have been plasma treated to cause the surface to be hydrophilic, or any other material or device that is capable of separating liquid from a fluid stream, or that is otherwise capable of substantially preventing the passage of liquid while allowing the passage of gases.

In accordance with one embodiment, the canister 102 includes an elongated member 162 that forms a conduit that allows gaseous communication between the liquid collection chamber 104 and the canister outlet 156 for maintaining reduced pressure in the liquid collection chamber 104 while substantially preventing liquid communication. The term "elongated" as used herein generally refers to a portion having notably a longer length than width. The elongated member 162 may have a membrane or a wall that defines the gaseous communication space. The elongated member 162 and thus the membrane or wall of the elongated member may be rigid, semi-rigid, rigid-in-sections, and/or flexible. For example, in some embodiments, the elongated member 162 may be pre-shaped such as with a foil or heat-formed plastic sheet to fit the canister 102 or any other canister design. In other embodiments, elongated member 162 may extend naturally based on an orientation of the canister 102. The term "flexible" as used herein generally means capable of being bent or shaped. In some embodiments, the shaping of the elongated member may not involve plastic deformation of any components of the elongated member, but in other embodiments, one or more elements of the elongated member may be plastically deformed such that the elongated member retains its shape after being manipulated and positioned within the canister. In some embodiments, the term "flexible" may refer to the ability of the elongated member to conform or be conformed to different shapes or arrangements within the canister without the use of special tools or equipment, such as for example by hand placement. In some embodiments, the elongated member 162 may include one or more portions/segments spaced along the membrane that allow the gaseous communication between the liquid collection chamber 104 and the canister outlet 156. In other embodiments, the membrane may substantially comprise a material that allows gaseous communication, but substantially prevents liquid communication.

In one embodiment, the elongated member 162 is connected to the substantially planar liquid-air separator 160 such that fluid communication is provided between the outlet 156 and the interior space of the elongated member 162. For example, the elongated member 162 may be welded to the liquid-air separator 160. In other embodiments, the elongated member 162 may be connected to the substantially planar liquid-air separator 160 using an adhesive material or by any other suitable means. Alternatively, in some embodiments, the substantially planar liquid-air separator 160 and the elongated member 162 are not separate components, but rather may be manufactured as a substantially unitary liquid-air separator. When coupled, the substantially planar liquid-air separator 160 and the elongated member 162 serve the same liquid-air-separation purpose of allowing air to move from the canister 102.

In certain embodiments, the canister 102 may also include an absorbent material for absorbing exudate and other fluids drawn from the tissue site 101. Additionally, the canister 102 may include a solidification substance such as isolyzer. Isolyzer reacts with a serum, plasma, tissue and organ homogenates, blood, or other water containing infectious liquids to form a solid substance.

FIG. 3 illustrates an embodiment depicting the liquid-air separator 160 and the elongated member 162 connected to one another and to the lid portion 146 of the canister 102. The liquid-air separator 160 is substantially planar to the lid portion 146. It should be noted that the shape and size of the liquid-air separator 160 may change depending on the shape and size of the lid portion 146, the outlet 156, or the recessed region 158 of the lid portion 146.

In one embodiment, the elongated member 162 is substantially perpendicular to the substantially planar liquid-air separator 160. However, in other embodiments, the elongated member 162 may be parallel to the substantially planar liquid-air separator 160 or connected at any angle at the point of attachment. The elongated member 162 extends away from the substantially planar liquid-air separator 160 and into the liquid collection chamber 104 of the canister 102. The elongated member 162 may be of varying length and width depending upon the size and configuration the canister 102. The elongated member 162 may be comprised of the same material as the liquid-air separator 160, as described above, or may be made of any other material that is capable of substantially preventing the passage of liquid while allowing the passage of gas. However, the elongated member 162 does not allow gaseous communication through portions of the elongated member 162 which are currently covered with liquid. Therefore, in the disclosed embodiments, the elongated member 162 is advantageously positioned, shaped, and/or manufactured to cover multiple planes within the liquid collection chamber 104 so as to enable the canister 102 to continue to receive reduced pressure from the reduced pressure source 108 in multiple, if not all, orientations of the canister 102. In addition to operating in multiple orientations, the elongated member 162 also enables continued air flow when there is fluid slosh that temporarily blocks exposed portions of the elongated member 162.

Additionally, in some embodiments, the elongated member 162 may comprise substantially of a liquid-air separator material. In another embodiment, the elongated member 162 may have one side that is liquid and gas impermeable, while the other side may comprise substantially of a liquid-air separator material. In yet another embodiment, the elongated member 162 may contain optimally placed portions that are liquid-air separators while the remaining portion of the elongated member 162 is liquid and gas impermeable. Still, in another embodiment, the elongated member 162 may include spaced apertures, and each of the apertures may be covered by a liquid-air separator. The above configurations of the elongated member 162 are provided as examples of certain embodiments. However, it should be noted that other embodiments of the elongated member 162 may be alternatively configured as to enable gaseous communication while substantially preventing liquid communication through the elongated member 162.

Figure 4A:
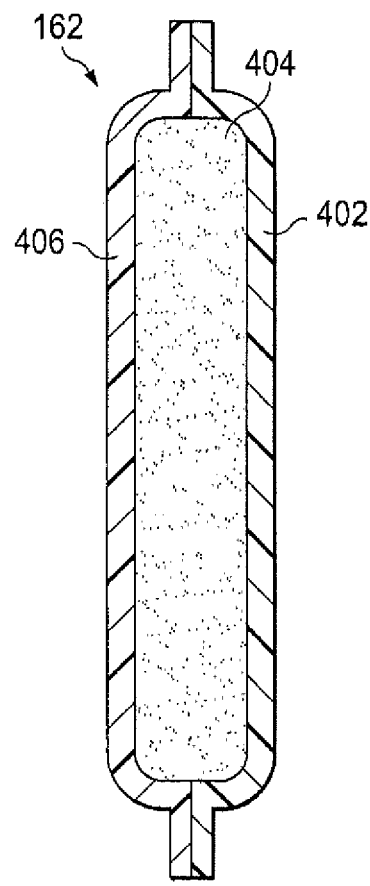
FIG. 4A illustrates a cross-sectional view of the filter element of FIG. 3 taken at 4-4.

For example, FIG. 4A illustrates a cross-sectional view of the elongated member 162 of FIG. 3 taken along line 4-4 in accordance with an illustrative embodiment. The elongated member 162 may consist of a first portion 402 welded or bonded to a second portion 406. Both the first portion 402 and the second portion 406 prevents, or substantially prevents, the passage of liquid (e.g., exudate) from the liquid collection chamber 104 into the inner portion, or gas communication pathway, of the elongated member 162. For instance, in one embodiment, the first portion 402 and the second portion 406 are hydrophobic membranes. Alternatively, the first portion 402 and the second portion 406 may be any material coated with a hydrophobic material to make them substantially impermeable to liquid.

In addition, at least one of the first portion 402 and the second portion 406 allows gaseous communication between the inner portion, or gas communication pathway, of the elongated member 162 and the liquid collection chamber 104. In one embodiment, at least one of the first portion 402 and the second portion 406 may be manufactured using polytetrafluoroethylene (PTFE), expanded polytetrafluoroethylene (ePTFE), or other fluoropolymer products. For example, in one embodiment, both the first portion 402 and the second portion 406 may be made of an ePTFE membrane manufactured by W.L Gore and Associates, Inc. for enabling gaseous communication between the inner portion of the elongated member 162 and the liquid collection chamber 104 while substantially preventing the passage of liquid. The first portion 402 and the second portion 406 may be joined by a weld, by an adhesive material, and/or by any other suitable means for providing a leak-free connection. Alternatively, in some embodiments, the first portion 402 and the second portion 406 may be manufactured as a single unit. For example, in one embodiment, the first portion 402 and the second portion 406 may be a folded sheet that is joined along a single seam.

Figure 4B:
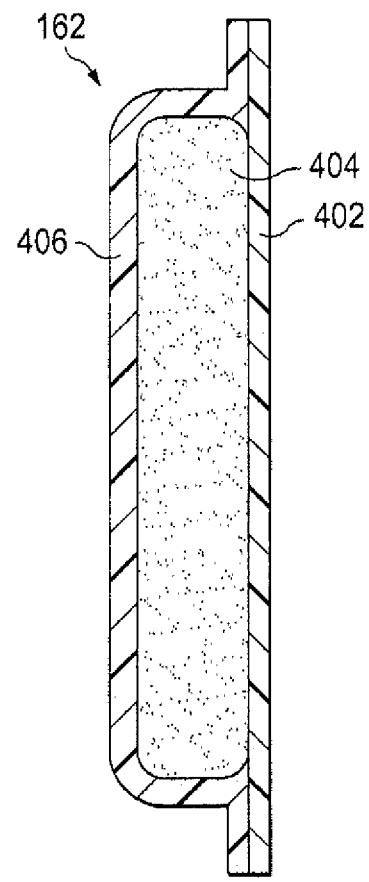
FIG. 4B illustrates a cross-sectional view of a filter element according to an illustrative embodiment, the cross-section view similar to that of FIG. 4A.

In another embodiment, as depicted in FIG. 4B, either the first portion 402 or the second portion 406 may be made of a material that prevents both gaseous and liquid communication, while the other of the first portion 402 or the second portion 406 is made of a material that allows gaseous communication, but substantially prevents liquid communication. Such a configuration may be less expensive than forming the entire elongated member 162 from gas permeable, liquid impermeable material.

Referring still to FIGS. 3, 4A, and 4B, the elongated member 162 may include a manifold or a biasing member 404 disposed within the conduit between the first portion 402 and the second portion 406 to reduce collapse of the elongated member 162 when exposed to reduced pressure. In one embodiment, the biasing member 404 may include a plurality of flow channels to manifold gas flow along the length of the elongated member 162. The biasing member 404 may be made of a non-woven material, such as, but not limited to, Libeltex™ TDL2, manufactured by Libeltex Group. Non woven materials include a range of polyolefin's, polyesters, and acrylics (and blends and laminates) that may be formed by melt blown, air laid, thermo and spun bonded techniques, and include such suppliers as Libeltex, Freudenberg, Buckeye, and Fiberweb. In other embodiments, the biasing member 404 may be made of a woven material; or Granufoam. Woven or textile material includes polyolefin, polyester, acrylics, polyurethanes, and polyamide based fibers, and blends and co-component fibers. Example manufacturers include DuPont, Eastman, and Atex. The biasing member may be formed from a compressible material, or alternatively from a rigid material such as for example by a lattice structure or other framework that is comprised of metal, plastic or other substantially rigid materials.

In addition, in some embodiments, the elongated member 162 may include an odor adsorption material (not depicted) within the conduit, such as, but not limited to, activated charcoal. Alternatively, and/or in addition to, an odor adsorption material may be placed between the connection of the substantially planar liquid-air separator 160 and the lid portion 146 of the canister 102.

Figure 5A:
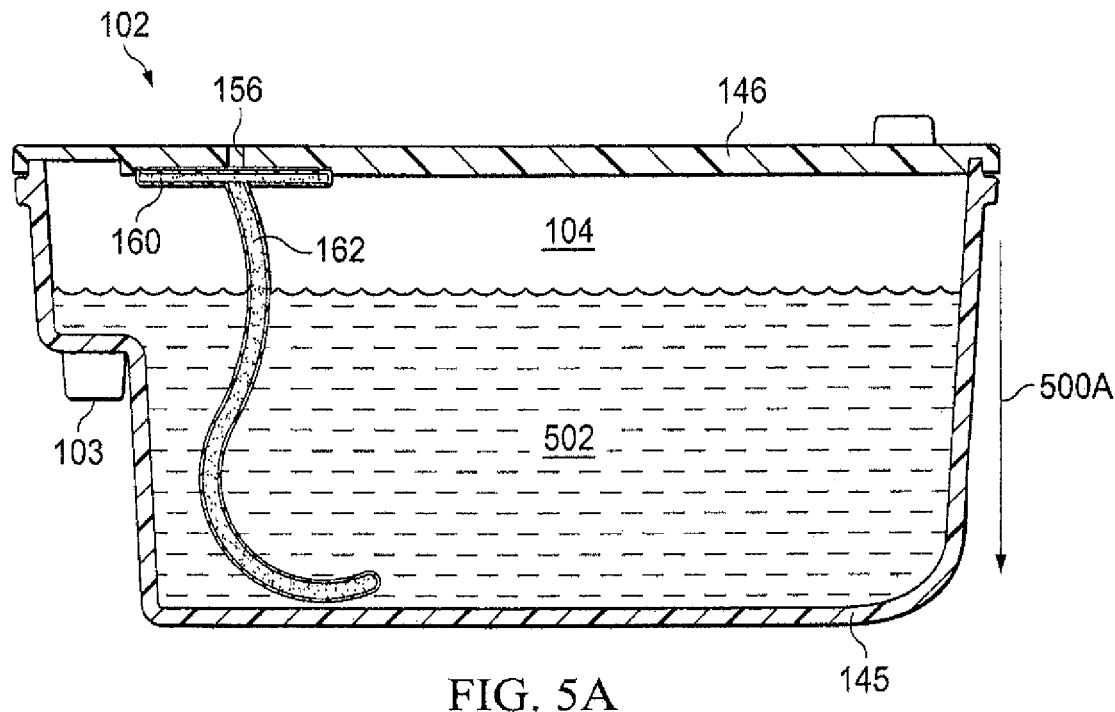
FIGS. 5A-5D illustrates different configurations of a filter element positioned in the liquid-collection canister of FIG. 2 according to an illustrative embodiment.

FIGS. 5A-5D illustrates different configurations of the elongated member 162 within the canister 102 of FIG. 1. In the depicted embodiment of FIG. 5A, the canister 102 is oriented such that gravity is asserted in the direction as indicted by arrow 500A. FIG. 5A illustrates the basin portion 145 connected to the lid portion 146 of the reduced pressure treatment unit 140 to form the liquid collection chamber 104. The substantially planar liquid-air separator 160 is connected to the recessed region 158 of the basin portion 145 to receive reduced pressure from the reduced pressure source 108 through the canister outlet 156. In one embodiment, the elongated member 162 is allowed to extend naturally into the liquid collection chamber 104 based on the direction of gravity. However, it should be noted that in some embodiments, the elongated member 162 may be formed, positioned, or manufactured, as to maintain the depicted shape no matter how the canister 102 is oriented.

As liquid 502 is collected in the liquid collection chamber 104, the portion of the elongated member 162 covered by the liquid 502 becomes blocked and does not allow gaseous communication between the inner space of the elongated member 162 and the liquid collection chamber 104. However, the remaining portion of the elongated member 162, or portions thereof, not covered by the liquid 502 enables gaseous communication between the inner space of the elongated member 162 and the liquid collection chamber 104 for providing reduced pressure from the reduced pressure source 108. As shown in FIG. 5A, under this orientation of the canister 102 and configuration of the elongated member 162, the liquid collection chamber 104 would continue to receive reduced pressure until the liquid collection chamber 104 is substantially full of liquid.

Figure 5B:
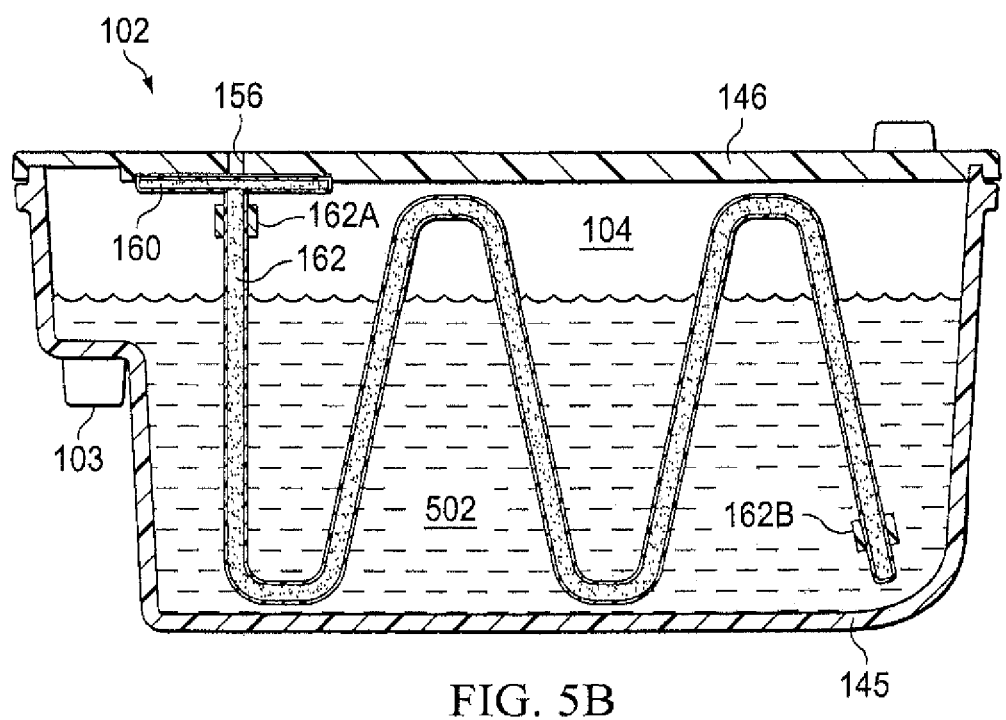
Figure 5C:
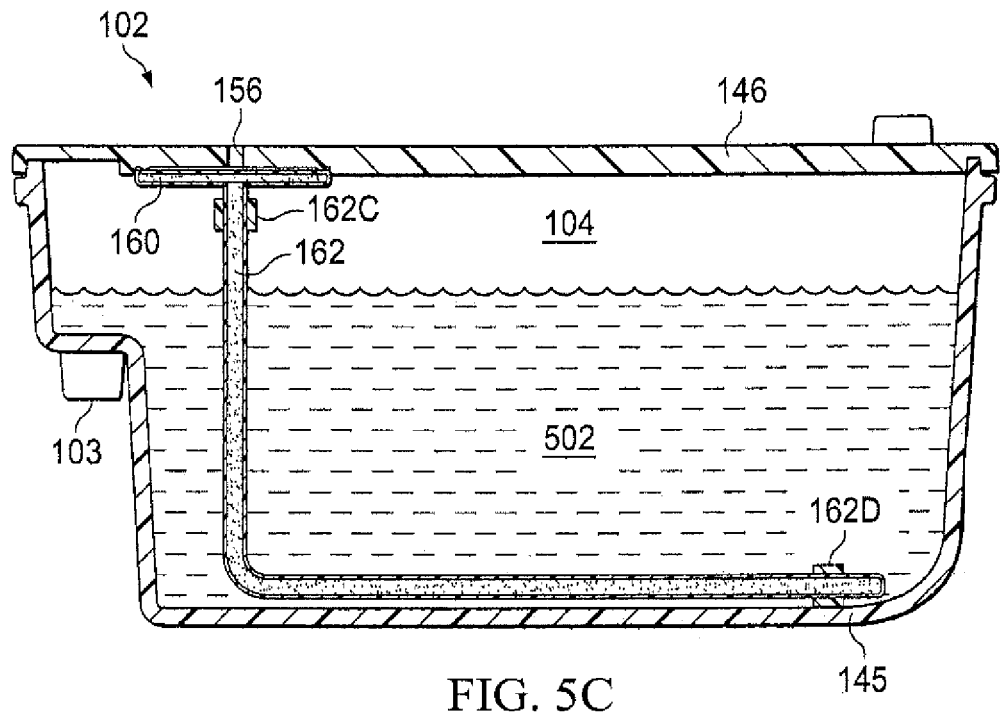
Figure 5D:
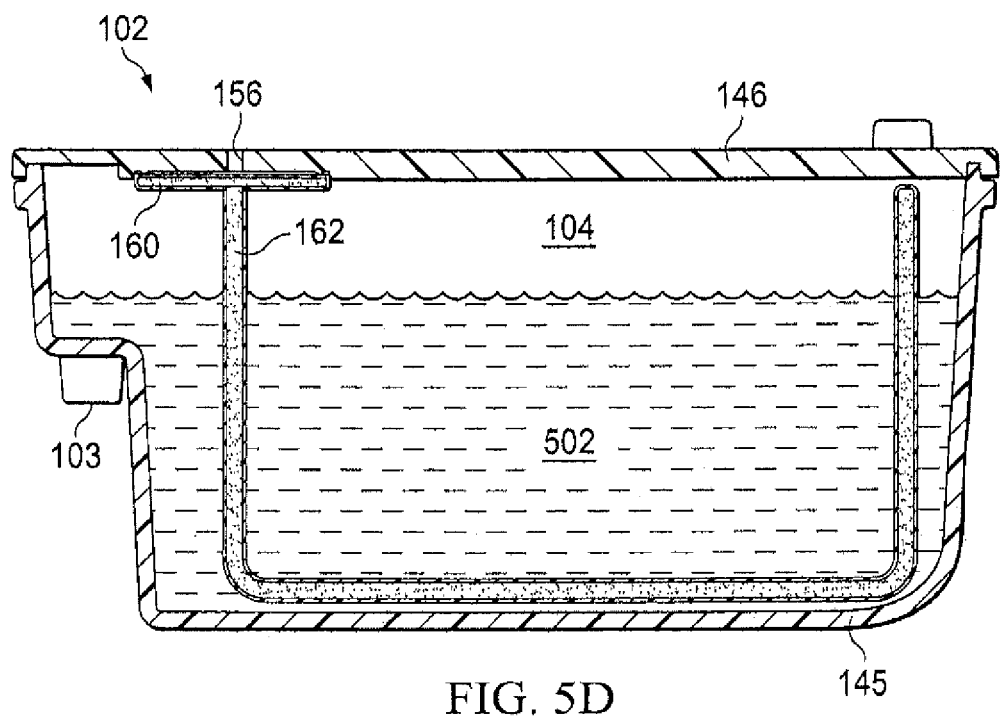

FIGS. 5B-5D illustrates other embodiments in which the elongated member 162 is positioned, shaped, or manufactured in a particular shape as to optimally fill the liquid collection chamber 104 in substantially any orientation of the canister 102 while maintaining reduced pressure in the liquid collection chamber 104. For instance, FIG. 5B illustrates an embodiment in which the elongated member 162 is positioned, shaped, or manufactured to extend into the liquid collection chamber 104 in an undulating configuration. As referenced herein, the term undulating refers to a wave-like configuration. In FIG. 5B, the canister 102 is oriented such that gravity is asserted in the direction as indicated by the arrow 500A (as shown in FIG. 5A). Therefore, as liquid 502 enters the liquid collection chamber 104, the liquid level would start covering the bottom portions of the elongated member 162 preventing gaseous communication through the covered portions of the elongated member 162. However, the uncovered upper portions of the elongated member 162 would continue to provide reduced pressure to the liquid collection chamber 104. Because the elongated member 162 is configured in such a way that extends substantially the width of the liquid collection chamber 104, the liquid collection chamber 104 continues to receive reduced pressure until the liquid collection chamber 104 is substantially full.

Figure 6A:
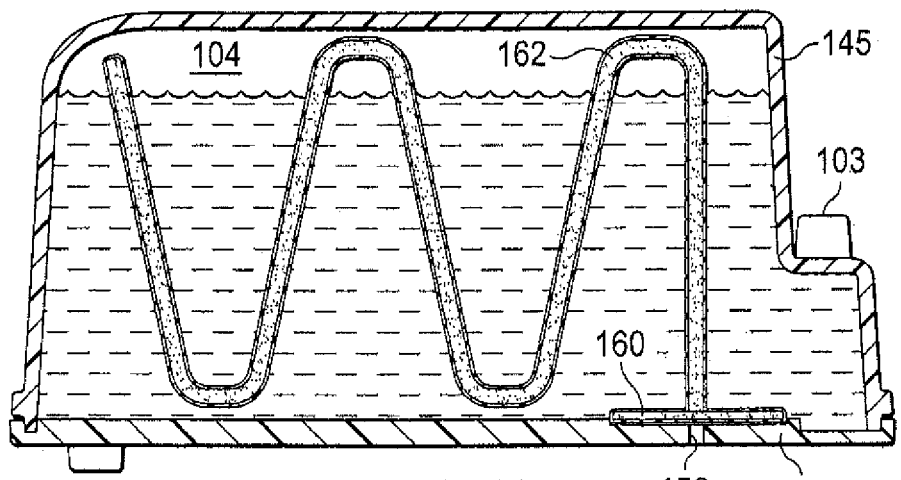
FIGS. 6A-6C illustrates different orientations of a liquid-collection canister having the filter configuration illustrated in FIG. 5B.
Figure 6B:
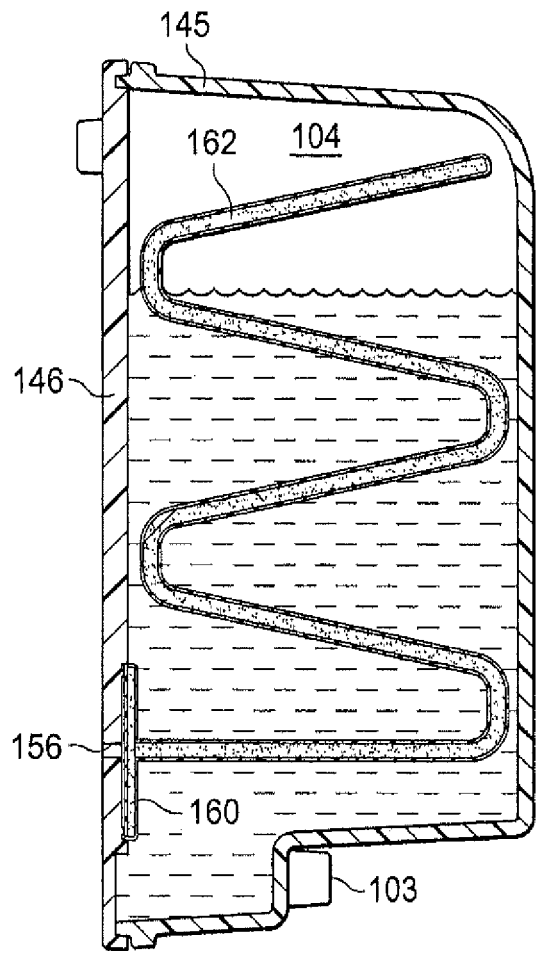
Figure 6C:
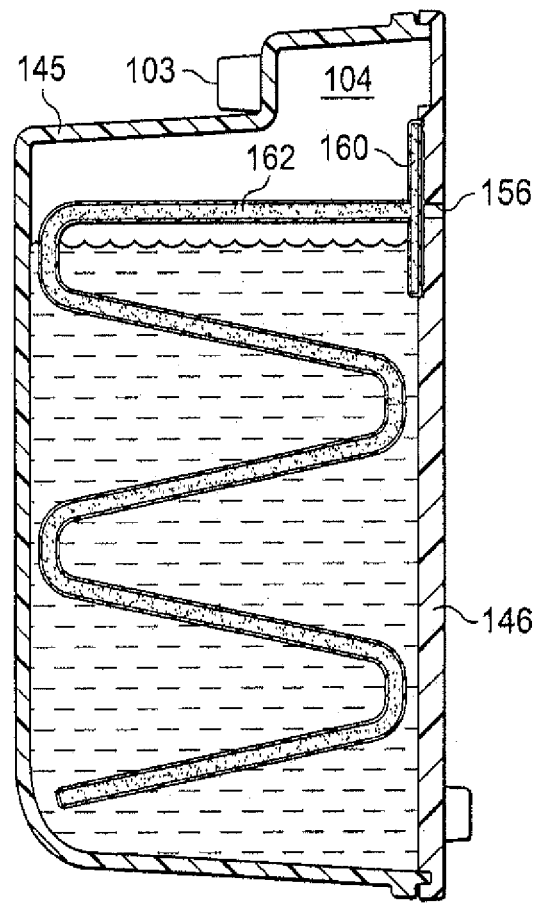

Additionally, because the elongated member 162 undulates to substantially cover the area of the liquid collection chamber 104, the canister 102 may be oriented in substantially any direction, and the liquid collection chamber 104 would still be able to receive reduced pressure until the canister 102 is substantially full. For example, FIGS. 6A-6C illustrates different orientations of the canister 102 having the filter configuration illustrated in FIG. 5B. As can be seen in the examples illustrated in FIGS. 6A-6C, no matter how the canister 102 is oriented, at least a portion of the elongated member 162 is not covered by the liquid 502 that allows for gaseous communication. Therefore, using the undulating configuration of the elongated member 162 as depicted in FIGS. 6A-6C, the canister 102 is able to maintain reduced pressure in the liquid collection chamber 104 until the liquid collection chamber 104 is substantially full.

In addition, referring back to the undulating configuration of FIG. 5B, the liquid collection chamber 104 would continue to receive reduced pressure until the canister 102 is substantially full even if only portions (e.g., at locations 162A and 162B) of the elongated member 162 provide gaseous communication, while the remaining portion of the elongated member 162 is both gas and liquid impermeable.

FIG. 5C illustrates another embodiment in which the elongated member 162 is positioned, shaped, or manufactured within the liquid collection chamber 104 to enable the canister 102 to fill with liquid in substantially any orientation while maintaining reduced pressure in the liquid collection chamber 104. For instance, in the depicted embodiment of FIG. 5C, the elongated member 162 is configured in an "L" shape formation that extends substantially the width and length of the liquid collection chamber 104. Again, the liquid collection chamber 104 would continue to receive reduced pressure until the canister 102 is substantially full even if only portions 162C and 162D of the elongated member 162 provide gaseous communication, while the remaining portion of the elongated member 162 is both gas and liquid impermeable. However, it should be noted that the elongated member 162 may comprise substantially of a liquid-air separator material or may include additional portions/segments beyond portions 162C and 162D of the elongated member 162 that provide gaseous communication, while substantially preventing liquid communication.

FIG. 5D depicts yet another embodiment in which the elongated member 162 is positioned, shaped, or manufactured within the liquid collection chamber 104 to enable the canister 102 to fill with liquid in substantially any orientation while maintaining reduced pressure in the liquid collection chamber 104. In the depicted embodiment of FIG. 5D, the elongated member 162 is configured in a "U" shape formation that extends substantially the width and length of the liquid collection chamber 104. The depicted embodiment of FIG. 5D provides several advantages over the prior art. For instance, the "U" shape formation may provide more stability to the elongated member 162 by enabling attachment of both ends of the elongated member 162 to the lid portion 146 of the reduced pressure treatment unit 140. This may be particularly advantageous in embodiments in which the reduced pressure treatment unit 140 is mobile unit such as when worn or carried by a patient. In addition, in some embodiments, both ends of the elongated member 162 may be attached to dual canister outlets (not shown) for providing reduced pressure to the canister 102 through multiple outlet ports.

Figure 7:
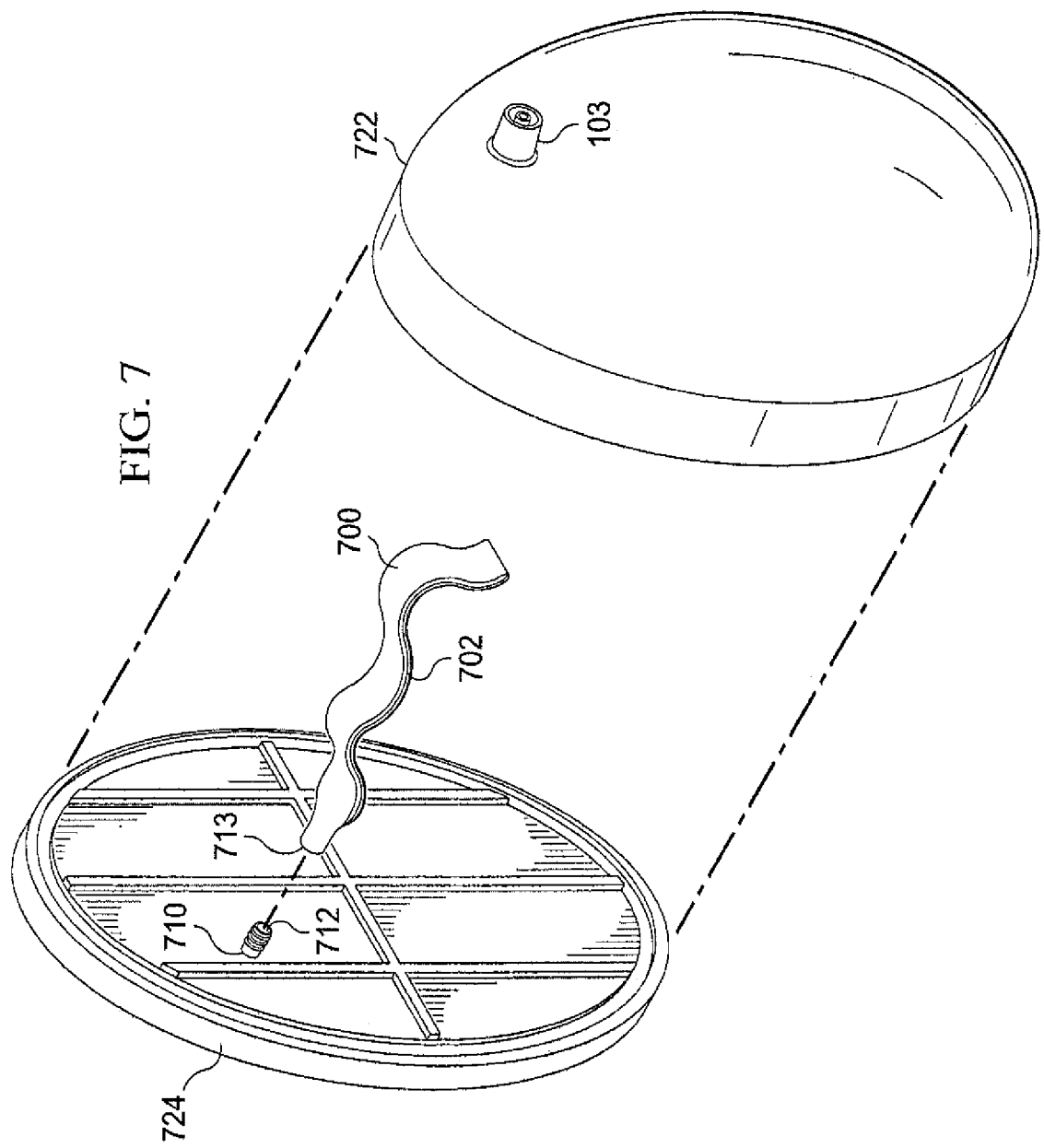
FIG. 7 illustrates a liquid-collection canister having a barb connector for connecting a filter element according to an illustrative embodiment.
Figure 8:
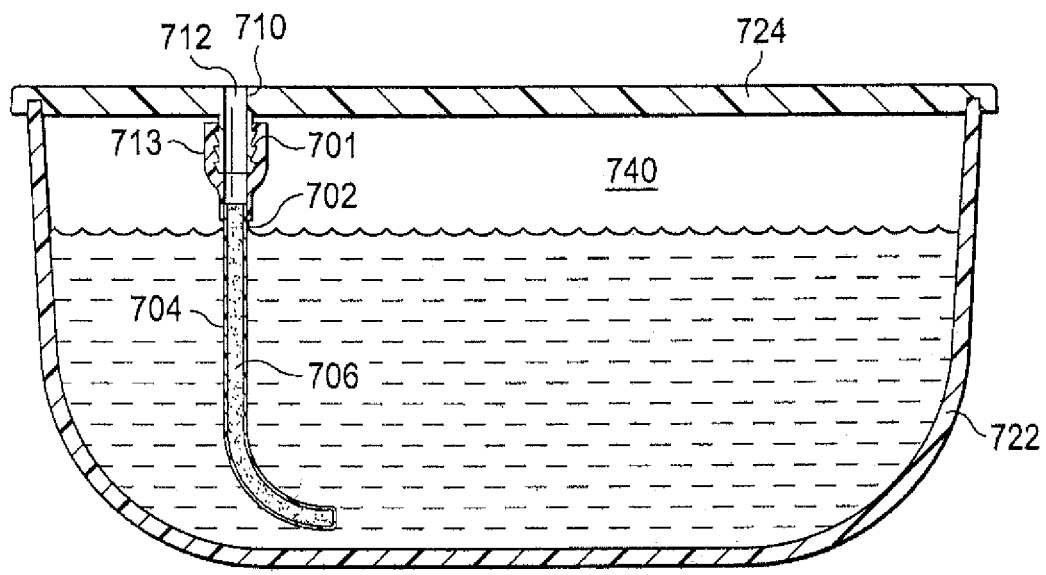
FIG. 8 illustrates a cross-sectional side view of the filter element and barb connector of FIG. 7 according to an illustrative embodiment.

Referring now to FIGS. 7 and 8, another embodiment of an elongated member 700 is provided. Beginning with FIG. 7, a generic canister 720 having a barb connector 710 for connecting the elongated member 700 to the canister 720 is illustrated according to an illustrative embodiment. The canister 720 includes a basin portion 722 that forms a liquid collection chamber 740 when connected to a canister wall 724 of the canister 720. The basin portion 722 includes an inlet 730 for transferring reduced pressure to a tissue site (not shown) and for receiving fluid from the tissue site.

In a preferred embodiment, the barb connector 710 may be formed as an integral part of the canister wall 724. The barb connector 710 is not limited to any particular location on the canister wall 724, and may be of varying size, shape, thickness, and depth depending on the particular design of the canister 720. In addition, in some embodiments, the canister wall 724 may include multiple barb connectors for connecting one or more of the elongated member 700 to different locations of the canister wall 724. In one embodiment, the barb connector 710 forms a hollow gas communication lumen 712 for receiving reduced pressure from the reduced pressure source 108. Although FIGS. 7 and 8 illustrate a barb type connector, the elongated member 700 may be coupled to the canister wall 724 by other means, including using other types of connectors and/or fasteners such as a clamp, adhesively bonding or welding the elongated member 700 to the canister wall 724, or by any other means for attaching the elongated member 700 to the canister wall 724.

The elongated member 700 is completely sealed except at an open end 713. The elongated member 700 connects to the barb connector 710 through the open end 713 for receiving reduced pressure through the barb connector 710. The elongated member 700 forms a conduit that is shaped, positioned, and/or manufactured to extend into the space of the liquid collection chamber 740 so as to provide optimum coverage for providing reduced pressure to the liquid collection chamber 740.

The elongated member 700 has a conduit wall 702 that forms a gas communication lumen 704 for transferring reduced pressure received from the reduced pressure source to the liquid collection chamber 740. The conduit wall 702 is substantially liquid impermeable. However, at least a portion the conduit wall 702 allows gaseous communication between the gas communication lumen 704 and the liquid collection chamber 740. In some embodiments, substantially the entire portion of the conduit wall 702 may allow gaseous communication between the gas communication lumen 704 and the liquid collection chamber 740, while substantially preventing liquid communication. The conduit wall 702 may be made of the same or similar material as previously described above with regard to the elongated member 162. For example, the conduit wall 702 may be made using expanded polytetrafluoroethylene (ePTFE) or any other suitable material that enables gaseous communication while substantially preventing liquid exchange. The conduit wall 702 may be formed as a single unit or by connecting multiple components/structures together using any suitable connection means such as welding or adhesive. The length, width, and thickness of the conduit wall 702 may vary depending on the particular configurations of the canister 720 so as to provide the optimum use of the liquid collection chamber 740 while maintaining reduced pressure. Additionally, the elongated member 700 may be configured within the liquid collection chamber 740 in any configuration as to optimally provide reduced pressure to the liquid collection chamber 740 such as, but not limited to, the configurations illustrated in FIGS. 5A-5D.

In some embodiments, the gas communication lumen 704 is an empty space in which reduced pressure can flow. In other embodiments, the gas communication lumen 704 may include a biasing member 706, such as, but not limited to, a non-woven material. The biasing member 706 may provide structural support to reduce collapse of the conduit wall when the gas communication lumen 704 is exposed to reduced pressure. The biasing member 706 may include a plurality of flow channels to manifold gas flow along the length of the gas communication lumen 704. In addition, in some embodiments, an odor adsorption material such as activated charcoal may be added to the biasing member 706 to absorb odor.

FIG. 8 illustrates a cross sectional side view of the elongated member 700 connected the barb connector 710 according to an illustrative embodiment. In one embodiment, the elongated member 700 may be attached to the barb connector 710 simply by pushing the barb connector 710 into the open end 713 of the elongated member 700. In some embodiments, the inner portion of the open end 713 may include integrated grooves or ridges 701 for enabling the open end 713 of the elongated member 700 to securely grip the barb connector 710. The open end 713 may be manufactured to have any particular size, shape, or thickness depending on the size and/or shape of the barb connector 710 so as to provide a tight leak-free connection. For example, the open end 713 of the elongated member 700 may be circular, oval, triangular, square, or any other shape that provides an optimal leak-free connection. In some embodiments, an adhesive, weld, clamp, and/or any other material may be applied to the connection to assist in providing a secure leak-free connection between the open end 713 of the elongated member 700 and the barb connector 710.

Figure 9:
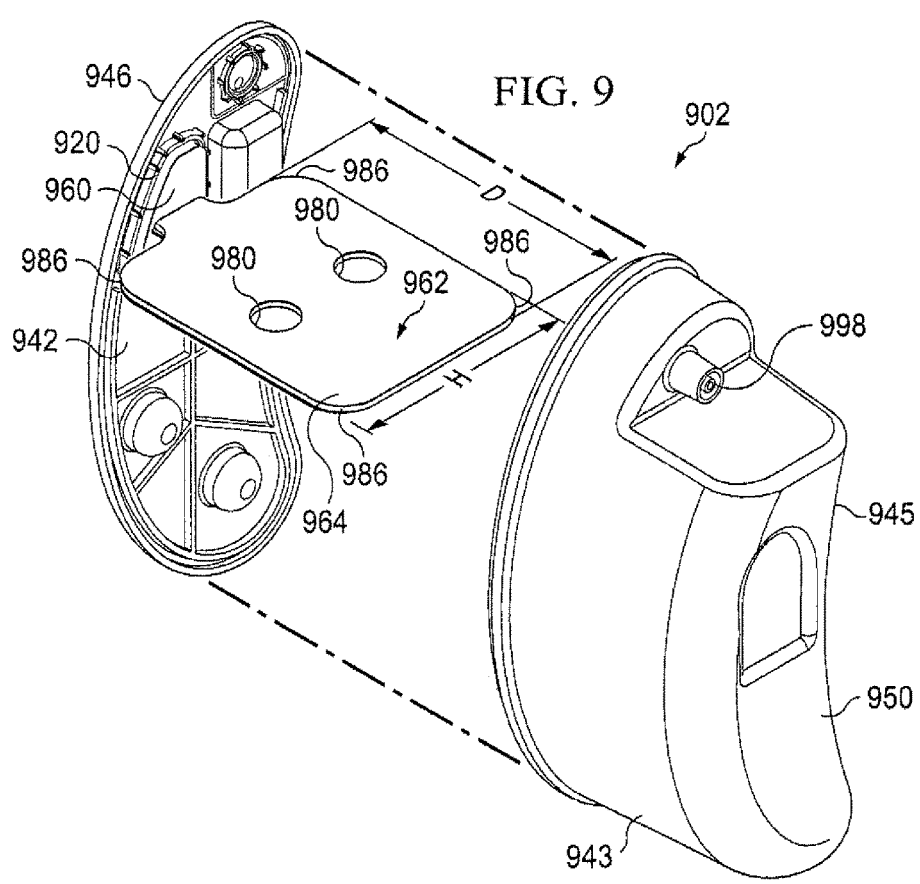
FIG. 9 illustrates an exploded perspective view of a liquid-collection canister according to an illustrative embodiment.

Referring to FIG. 9, a canister 902 similar to canister 102 (FIG. 3) or canister 720 (FIG. 7) includes a canister housing 943 having a basin portion 945 and a lid portion 946. The lid portion 946 may be formed by an exit wall 942 that is substantially planar and is capable of mating with the basin portion 945 to form a liquid collection chamber. While the basin portion 945 is formed from a basin wall 950 that includes curved contours to create a crescent shape, the basin portion 945 and lid portion 946 may instead form a canister that is cylindrical, cubical, spherical, rectangular cubical, or any other shape. It should also be noted that the canister 902 may not include separate basin and lip portions, but rather may be formed from a substantially unitary housing. In such an embodiment, the liquid-collection chamber may be defined by a single wall. Alternatively, the liquid-collection chamber may be formed by a plurality of walls.

Similar to canister 102 of FIG. 3, canister 902 includes an inlet 998 that is configured to be fluidly connected to a conduit, and a canister outlet 920 that is fluidly connected to a reduced pressure source. A substantially planar liquid-air separator 960 is operatively associated with the outlet 920 of the canister 902 to prevent liquid from exiting the canister 902 through the canister outlet 920. In one embodiment, the outlet 920 is positioned in the exit wall 942, and the substantially planar liquid-air separator 960 is positioned adjacent to the outlet and secured to the exit wall 942. The substantially planar liquid-air separator 960 prevents liquids that that are drawn into the canister 902 from exiting the canister 902 through the outlet 920 and contaminating the reduced pressure source. In an illustrative embodiment, the substantially planar liquid-air separator 960 may be a hydrophobic or oleophobic filter as described previously with reference to liquid-air separator 160.

In accordance with one embodiment, the canister 902 includes a dividing member 962 that forms a conduit that allows gaseous communication between the liquid collection chamber and the canister outlet 920 for maintaining reduced pressure in the liquid collection chamber while substantially preventing liquid communication. The dividing member 962 includes a wall 964 or membrane that defines a gas-communication pathway or space similar to that described previously with reference to the elongated member 162 illustrated in FIGS. 4A and 4B. The wall 964 of the dividing member 962 and the dividing member 962 itself may include the same flexible, or alternatively, rigid characteristics of the elongated member 162. At least a portion of the wall 964 is formed from a material that allows gaseous communication between the gas-communication space of the dividing member 962 and the liquid collection chamber of the canister 902. The wall 964 or membrane may be formed from a unitary piece of material, or from two or more pieces of material that are welded, bonded, or otherwise attached together. The gas-communication space may include a biasing material similar to that previously described with reference to elongated member 162.

The shape of the dividing member 962 is such that it closely matches an interior profile of the liquid collection chamber of the canister 902, and the dividing member may include a width, W, and a depth, D, that is substantially equal to a corresponding width and depth of the canister housing 943. This particular shaping and sizing of the dividing member 962 is such that the dividing member 962 substantially divides the liquid collection chamber of the canister housing 943 into first and second chambers or spaces. In the embodiment illustrated in FIG. 9, the division of the liquid collection chamber would result in an upper chamber positioned above the dividing member 962 and a lower chamber below the dividing member 962.

The dividing member 962 may serve to prevent excessive liquid movement or sloshing within the liquid collection chamber since the liquid collection chamber is substantially divided. The dividing member 962 may include at least one aperture 980 through the wall of the dividing member 962 to allow fluid communication between the upper chamber and the lower chamber of the liquid collection chamber. The placement of the apertures 980 in the dividing member 962 still maintains the sealed integrity of the gas-communication space within the dividing member 962 such that liquid is not able to enter the gas-communication space.

The dividing member 962 is connected to the substantially planar liquid-air separator 960. For example, the dividing member 962 may be welded to the liquid-air separator 960. In other embodiments, the dividing member 962 may be connected to the substantially planar liquid-air separator 960 using an adhesive material or by any other suitable means. Alternatively, in some embodiments, the substantially planar liquid-air separator 960 and the dividing member 962 are not separate components, but rather may be manufactured as a substantially unitary liquid-air separator. When coupled, the substantially planar liquid-air separator 960 and the dividing member 962 serve the same liquid-air-separation purpose of allowing air to move from the canister. In still other embodiments, a substantially planar liquid-air separator 960 may not be used, and the dividing member 962 may be directly connected to the outlet 920 of the canister 902 such that the gas-communication space is in fluid communication with the outlet of the canister 902.

Besides the connection of the dividing member 962 to the liquid-air separator 960 or the outlet of the canister 902, the dividing member 962, in any particular embodiment, may be connected to the canister 902 at other locations around the perimeter of the dividing member 962. For example, in the embodiment illustrated in FIG. 9, the dividing member 902 may be connected at each of four corners 986 to one or more walls of the canister 902. This supplemental attachment of the dividing member 962 to the canister 902 may serve to increase the ability of the dividing member 962 to maintain the divided nature of the liquid collection chamber. In other embodiments, the dividing member 962 may not be attached to the canister 902 at locations other than the outlet of the canister 902.

While only a few canister shapes have been illustrated and described, use of the filters or elongated elements described herein, and the advantages that these filters and elongated elements provide, is not limited to any particular shape of canister. In addition, each of the filters and elongated elements described herein may be varied in size or shape to better accommodate a canister of a particular size or shape.

While some of the filters presented herein have been described as having a single interior space or chamber, the number of filter chambers is not limited. Multiple filter chambers that are either independently or jointly connected to the canister outlet or multiple canister outlets may be employed, again depending at least partially upon the size and shape of the canister. Similarly, multiple filter elements may be used to increase the time that the filter maintains gas transmission during liquid collection activities.

The filters and liquid-collection canisters described herein may be used as part of a process or method for retrofitting an existing wound fluid collection canister design or a new wound collection canister design to allow collection of wound fluid in multiple orientations of the wound fluid collection canister. The method includes fluidly connecting an elongated member to an outlet of the wound fluid collection canister. At least a portion of the elongated member extends into a liquid collection area of the wound fluid collection canister. The method further includes allowing gas exchange between an inner space of the elongated member and the liquid collection area; and substantially preventing liquid exchange between the inner space and the liquid collection area. In some embodiments, the method may further include undulating, shaping, positioning, and/or manufacturing the portion of the conduit extending into the liquid collection area of the wound fluid collection canister such that gas exchange between the inner portion of the conduit and the liquid collection area is optimally maintained.

It should be apparent from the foregoing that an invention having significant advantages has been provided. While the invention is shown in only a few of its forms, it is not just limited but is susceptible to various changes and modifications without departing from the spirit thereof.

While a number of discrete embodiments have been described, aspects of each embodiment may not be specific to only that embodiment and it is specifically contemplated that features of embodiments may be combined with features of other embodiments.

We claim:

1. A canister for collecting liquid from a tissue site to which reduced pressure treatment is applied, the canister comprising:
   at least one canister wall defining a first space configured to collect liquid from the tissue site;
   a canister outlet configured to allow communication between a reduced pressure source and the first space;
   an elongated member fluidly connected to the canister outlet and extending away from the canister outlet into the first space, the elongated member having a membrane defining a second space along at least a portion of a length of the elongated member, at least a portion of the membrane allowing gaseous communication between the first space and the second space; and
   a biasing member surrounded by the membrane and configured to reduce collapse of the elongated member when the second space is exposed to reduced pressure.

2. The canister of claim 1, further comprising:
   a substantially planar, liquid-air separator disposed adjacent the canister outlet to prevent the liquid from exiting the first space through the canister outlet, the elongated member being connected to the substantially planar, liquid-air separator.

3. The canister of claim 1, wherein the elongated member is connected to the canister outlet using a hose barb attachment.

4. A canister for collecting liquid from a tissue site to which reduced pressure treatment is applied, the canister comprising:

a chamber configured to collect liquid from the tissue site;

a canister outlet in fluid communication with a reduced pressure source;

a flexible member having a gas communication pathway at least partially defined by a flexible membrane, the flexible member being positioned in the chamber such that the gas communication pathway is in fluid communication with the canister outlet, at least a portion of the flexible membrane being gas permeable and substantially liquid impermeable; and a manifold surrounded by the flexible member and configured to support the flexible member under reduced pressure.

5. The canister of claim 4, further comprising a substantially planar, liquid-air separator connected to a wall of the canister to substantially cover the canister outlet, the flexible member being connected to the substantially planar, liquid-air separator.

6. The canister of claim 5, wherein the flexible member and the liquid-air separator are a single unit.

7. The canister of claim 5, wherein the flexible member is welded to the liquid-air separator.

8. The canister of claim 5, wherein the flexible member is adhesively bonded to the liquid-air separator.

9. The canister of claim 4, wherein the flexible member is connected to the canister outlet using a hose barb attachment.

10. The canister of claim 4, wherein the flexible member is connected to the canister outlet using a clamp.

11. The canister of claim 1, wherein the biasing member is configured to manifold gas flow through the second space under reduced pressure.

12. The canister of claim 1, wherein the biasing member includes a plurality of flow channels.

13. The canister of claim 1, wherein the biasing member comprises a compressible material.

14. The canister of claim 1, wherein the biasing member comprises a nonwoven material.

15. The canister of claim 1, wherein the biasing member comprises a woven material.

16. The canister of claim 1, wherein the biasing member comprises an open-cell foam.

17. The canister of claim 1, wherein the elongated member and the biasing member are flexible within the first space.

18. The canister of claim 1, wherein the elongated member is configured to extend into the first space based on the direction of gravity.

19. The canister of claim 1, wherein the membrane prevents liquid communication between the first space and the second space.

20. The canister of claim 4, wherein the manifold is configured to manifold gas flow through the gas communication pathway under reduced pressure.

21. The canister of claim 4, wherein the manifold includes a plurality of flow channels.

22. The canister of claim 4, wherein the manifold comprises a compressible material.

23. The canister of claim 4, wherein the manifold comprises a nonwoven material.

24. The canister of claim 4, wherein the manifold comprises a woven material.

25. The canister of claim 4, wherein the manifold comprises an open-cell foam.

26. The canister of claim 4, wherein the flexible member and the manifold are flexible within the chamber.

27. The canister of claim 4, wherein the flexible member is configured to extend into the chamber based on the direction of gravity.

28. The canister of claim 4, wherein the flexible membrane prevents liquid communication between the chamber and the gas communication pathway.

29. A canister for collecting liquid from a tissue site to which reduced pressure treatment is applied, the canister comprising:

a chamber configured to collect liquid from the tissue site;

a canister outlet configured to allow communication between a reduced pressure source and the chamber;

an elongated member fluidly connected to the canister outlet and extending away from the canister outlet into the chamber, the elongated member having a first portion and a second portion, the first portion bonded to the second portion and forming a gas communication pathway, at least a part of the first portion being gas permeable; and a biasing member disposed in the gas communication pathway and configured to reduce collapse of the elongated member when the gas communication pathway is exposed to reduced pressure.

30. The canister of claim 29, wherein at least a part of the first portion is liquid impermeable.

31. The canister of claim 29, wherein at least a part of the second portion is gas and liquid impermeable.

32. The canister of claim 29, wherein the biasing member is configured to manifold gas flow through the gas communication pathway under reduced pressure.

33. The canister of claim 29, wherein the biasing member includes a plurality of flow channels.

34. The canister of claim 29, wherein the biasing member comprises a compressible material.

35. The canister of claim 29, wherein the biasing member comprises a nonwoven material.

36. The canister of claim 29, wherein the biasing member comprises a woven material.

37. The canister of claim 29, wherein the biasing member comprises an open-cell foam.

38. The canister of claim 29, wherein the elongated member and the biasing member are flexible within the chamber.

39. The canister of claim 29, wherein the elongated member is configured to extend into the chamber based on the direction of gravity.

40. The canister of claim 29, wherein the first portion and the second portion prevent liquid communication between the chamber and the gas communication pathway.

* * * * *